United States Patent [19]

Maples et al.

[11] Patent Number: 5,409,826
[45] Date of Patent: Apr. 25, 1995

[54] PRESERVED, NON-INFECTIOUS CONTROL CELLS PREPARED BY THE MODULATION OR MODIFICATION OF NORMAL CELLS

[75] Inventors: John A. Maples, Davie; Patricia A. Roth, Pembroke Pines; Melissa J. Stiglitz, North Miami Beach, all of Fla.

[73] Assignee: Coulter Corporation, Miami, Fla.

[21] Appl. No.: 73,937

[22] Filed: Jun. 8, 1993

[51] Int. Cl.⁶ .................. A01N 1/02; C12N 5/08; G01N 31/00
[52] U.S. Cl. .................. 435/240.2; 435/29; 435/2; 536/124; 436/10
[58] Field of Search .............. 436/10; 424/534, 3; 435/2, 29, 240.2; 536/124

[56] References Cited

U.S. PATENT DOCUMENTS

| | | | |
|---|---|---|---|
| 4,489,162 | 12/1984 | Hawkins et al. | 436/10 |
| 4,677,061 | 6/1987 | Rose et al. | 435/39 |
| 4,867,908 | 9/1989 | Recktenwald et al. | 252/408 |
| 4,876,189 | 10/1989 | Schetters et al. | 437/7 |
| 5,059,518 | 10/1991 | Kortright et al. | 435/6 |
| 5,256,534 | 10/1993 | Butera et al. | 435/5 |

OTHER PUBLICATIONS

Dustin M L et al, J. Immunol 137:245–54 (1986).
Evans H J et al, Nature 284:370–2 (1980).

*Primary Examiner*—Marian Knode
*Assistant Examiner*—Sandra Sancier
*Attorney, Agent, or Firm*—Michelle A. Kaye

[57] ABSTRACT

The invention describes the preparation of preserved, non-infectious control cells. The control cells are prepared by modification, activation or otherwise changing selected normal leukocyte cells, tissue culture cells or zenogenic transplants in immunosuppressed animals to have characteristics of abnormal cells or by the addition of cells from an established cell line, which has been similarly modified or activated, to a normal leukocyte population. The preferred method of preserving the control cells is by lyophilization using an isotonic 10% trehalose solution.

9 Claims, 7 Drawing Sheets

PRESERVED, NON-INFECTIOUS CONTROL CELLS PREPARED BY THE MODULATION OR MODIFICATION OF NORMAL CELLS

RELATED INVENTION

This application is related to U.S. Pat. No. 5,059,518, issued Oct. 22, 1991 and to application Ser. No. 07/944,678, filed Sep. 14, 1992, and entitled PRESERVED, NON-INFECTIOUS CONTROL CELLS FOR USE IN THE IDENTIFICATION OF A DISEASE THROUGH BLOOD TESTING. This application, U.S. Pat. No. 5,059,518 and application 07/994,678, now abandoned, are owned by a common assignee, Coulter Corporation, Hialeah, Fla.

FIELD OF THE INVENTION

This invention relates to control cells and a method of producing the same for use in clinical and immunological analytical procedures. Specifically, this invention relates to preserved, non-infectious control cells which are derived from peripheral blood cells or an established cell line. The cells are modified or changed to have the characteristics of abnormal cells. These control cells have, among the total population or count of cells in a given control cell sample, a population or count of at least one specific cell type which has an amount or degree of antigenic (antibody-binding) expression, or expression of cellular constituents (for example, enzymes or nucleic acids) that is characteristic of:

(1) abnormal peripheral blood cells obtained from a patient suffering from a disease, or
(2) normal hematologic tissue different from normal peripheral blood cells, such as, bone marrow cells and the cells derived therefrom, for example, red blood cells.

BACKGROUND OF THE INVENTION

Control cells are essential for the accuracy and precision of clinical and immunological assays. They are needed to insure the reliability and accuracy of test equipment and methods and to insure reproducibility through time and from laboratory to laboratory. State and federal regulations which govern such assays often require the use of multi-level controls in order to demonstrate that equipment is performing properly over a range of values. In immunological assays, fresh normal cells have been the standard control cells for such equipment testing. In order to avoid the cost and expense of obtaining and maintaining fresh cells, various methods of preserving fresh cells for use as control cells have been evaluated. For example, U.S. Pat. No. 5,059,518 (the '518 patent) describes the use of lyophilized normal cells for use as control cells.

Abnormal blood cell samples have also been used as controls to confirm the presence of a disease or to determine its stage, but their use has been restricted to fresh or refrigerated samples obtained from diseased patients. The supply of such samples is thus inherently restricted, inherently variable and of limited shelf life. Furthermore, since many of such blood samples are also associated with infectious diseases, they are not amenable, for health and social as well as sometimes technical reasons, to large scale production and distribution, and they require special handling procedures.

Some aspects of the problem may be overcome as disclosed in related application Ser. No. 07/944,678 which describes the use of control cells which reflect the abnormal extant state of a blood cell population arising from:

(1) an increase or decrease in the number of cells of a specific type due to the presence of a disease; or
(2) the presence of cells not normally found in normal blood samples, such cells being different in size, shape or other physical characteristics, or having thereon molecules and/or antigenic sites not found on the normal cells.

The control cells of the first type are prepared by depleting a blood sample of specific cells normally present in blood to less than normal levels or by adding such cells to above normal levels and subsequently preserving such samples. The control cells of the second type are prepared by the addition of cells not normally present in a normal blood sample to a normal blood sample and subsequently preserving such sample.

This invention describes a method of preparing, from normal cells or a combination of normal cells and a selected, established cell line, control cells which can be used as an alternative to abnormal cells obtained from patients. To make the control cells of the invention, normal cells obtained from disease free patients or cultured cells are obtained from an established cell line. These cells are subsequently modified, altered or changed to so that they reflect the characteristics of one or more specific cells types which would be present in the blood of a patient having a specific disorder or disease. The normal or cultured cells can also be modified to reflect the characteristics of certain cell types found in tissues as opposed to peripheral blood. For example, normal cells can be modified to reflect the antigenic characteristics of bone marrow cells and derivatives thereof.

The modulation or modification of cells to produce appropriate control cells is not limited to the expression of any one particular cellular constituent and represents a cascade of events reflected in changes in many constituents. Thus the modulation or modification of cells is performed to produce control cells that are appropriate for the constituent(s) being analyzed—be they antigenic constituents as tested by monoclonal antibody binding, enzymatic assays as determined by substrate modification or nucleic acid changes as demonstrated by DNA or RNA probes. The antigenically defined components are, therefore, the endpoint of a cascade of cellular events and the product of DNA/RNA directed biosynthesis.

SUMMARY OF THE INVENTION

The invention provides for mammalian cells which reflect a specific cell population in a blood or tissue sample of a mammal which has an disease, disorder or condition which manifests itself, among other ways, as a change in the expression in type, number or physicochemical properties of components present on or in cells. Antigenically defined components are antibody binding sites. Other components may consist of enzymes, and their active nucleic acid containing materials such as DNA or RNA, cellular macrostructures such as ribosomes and the configuration of nuclear components such as the nucleus. The invention further provides methods for producing such control cells.

The control cells described herein are produced from normal, non-infectious, non-disease-altered peripheral blood cells or from an established cell line by the use of known means to activate or modify the cell's own biosynthesis mechanisms. The control cells also can be produced by chemically or enzymatically modifying specific chemical groups on a cell or by inhibiting the expression of antigenically defined characteristics. The altered cells can be added to normal cells in selected amounts. Different amounts of specific cells in the peripheral blood of tissue sample is often reflective of the stage of a disease (how far it has progressed) or disorder (an abnormal physical condition).

The control cells are prepared by activating or inhibiting the cells own biosynthetic mechanisms, or chemically or enzymatically modifying the antigenically defined components in or on normal peripheral blood cells or cells from an established cell line; or by growing the cells in an immunosuppressed laboratory animal in which various biochemical reagents are used to modify cell growth. The normal blood cells or cells from an established cell line that have been so activated, modified, inhibited or grown can be preserved, for example, by lyophilization, so as to have an extended storage life. The control cells which are prepared and preserved according to the invention retain, after reconstitution, all the antigenicity and cell surface structural characteristics and cellular constituents of the corresponding fresh cells.

The expression of antigenically defined components is known to be a reflection of cellular DNA and RNA in association with the cell's biosynthetic structures. The detection of antigenically defined structures is the detection of the final products of a cascade of events. Detection is feasible at various stages in this process—be it DNA or RNA changes, or an alteration in various cellular enzymes or physical structures. Detection may be done using monoclonal antibodies, DNA and RNA probes, enzymes and other biological and chemical substance known to these skilled in the art.

The invention also provides for a process for preparing the preserved mammalian control cells. In the process selected leukocyte cells, tissue culture cells or zenogenic transplants in immunosuppressed animals are artificially activated and/or modified to express a characteristic expressed on similar cells in a person having a disease or disorder which results in the expression of the characteristics on the cells. The method comprises, for example using leukocyte cells, incubating a sample of normal leukocyte cells in a medium, typically a fluid or solution of suitable composition for the incubation, and in the presence of an enzyme or chemical reagent to selectively activate or modify the antigenic characteristics of a selected population of the leukocyte cells such that the selected population of cells has characteristics representative of the same cells in a patient suffering from a disease or disorder which results in the expression of such characteristics on the selected cells. The treated leukocyte cells are then separated from the medium and washed. After washing, the cells are preserved by a suitable preservation technique. The preferred preservation technique is lyophilization after suspension in an isotonic 10% trehalose solution.

DETAILED DESCRIPTION OF THE INVENTION

Definitions

Figure 1:
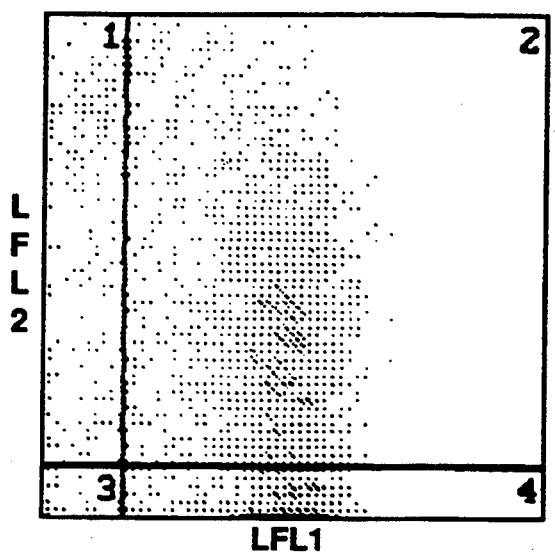
FIG. 1 is a histogram illustrating the distribution of normal peripheral blood lymphocytes activated with 3 $\mu$g/ml PHA for 36 hours.

The term "antigen modified control cell" signifies a control cell in which the expression of an antigen in a specific cell type or types differs from that in cells found in a normal blood sample or as expressed in cells found in hematological tissue other than normal blood.

The term "abnormal blood sample" refers to a blood sample taken from a patient suffering from a disease or disorder. The term "abnormal blood cells" or "abnormal cells" refers to those cells which exhibit antigenicity or structural characteristics different from normal cells as a result of a patient having a disease or disorder.

The terms "activated" or "artificially activated", "modified" or "artificially modified", "inhibited" or "artificially inhibited", and "altered" or "artificially altered", and the use of the word "artificial" in conjunction with another word signifying change, are used herein to distinguish cells which have altered characteristics, antigenically or otherwise as compared to normal cells, as a result of the use of chemical reagents, enzymes, radiation and other reagents either taught herein or known to those skilled in the art as effecting such changes. These cells are thus distinguished from cells which have the same characteristics due to their being obtained from a patient who has a disease or disorder which result in similar characteristics being present on cells.

All solution concentrations given herein are in weight percent unless specified otherwise.

Description

The claimed invention uses various means to activate, inhibit, or modify normal cells or cells cultured from an established cell line. Some of these methods have been described in the scientific and technical literature. W. Knapp et al., in a publication appearing in LEUKOCYTE TYPING IV, H. Stein and R. Schwarting, Eds. (Oxford University Press 1989), pages 384–513, report that processes which stimulate cells to proliferate results in a change in the expression of cellular antigens on those cells. D.T.Y. Yu et al., in a publication entitled "Peripheral blood Ia-positive T cells: Increases in certain diseases after immunization", J. Exp. Med. 151: 91–100 (1980), report that the activation of T lymphocytes causes an increase in the expression of type II MHC antigens on the T cells as would be seen on the cells of patients who have certain diseases or after patient immunization. Activation of normal peripheral blood T cells by known means such as certain plant lectins (PHA, PWA) crosslinked antibodies (CD3, CD11, CD28) modulates cellular antigens. That is, it increases the number of cells having the type II MHC antigens. As a result, cells which have been activated or modified to exhibit the MHC antigens can mimic the type of cells found in clinical situations. The activated or modified cells can be preserved and used as control cells for clinical and immunological analytical procedures.

C. I. Civing et al. report in LEUKOCYTE TYPING IV, op. cit., page 818, that in some patients suffering from acute myelogenous leukemia (AML), a peripheral blood sample will contain cells which have a CD34 antigen not present on normal blood cells. The enumeration of CD34 positive cells in bone marrow samples is used in bone marrow transplantation procedures to evaluate precursor cells populations. See BONE MARROW PROCESSING AND PURGING: A PRACTICAL GUIDE, A. P. Gee, Ed. (CRC Press, Boca Raton, Fla.), pages 145–148. The expression of CD34 on these cells is variable and is usually less than that seen in tissue culture cells, for example, KG1a cells, available from the American Type Culture Collection (ATCC), Rockville, Md., ATCC Deposit No. CCL 246.1. Modification of the CD34 antigen on cultured cells by chemical or enzymatic means can provide control cells which mimic the cellular expression of the antigen as seen under a variety of clinical conditions.

In order to identify a particular type of cell associated with a specific disease or condition, several different molecular structures may have to be identified on a single cell. A broad class of cells may have to be increasingly subdivided in to smaller and more specific subsets. In order to distinguish one broad class of cells within several broad classes of cells, and to further distinguish subsets within the selected broad class of cells, current technology uses selected monoclonal antibodies bearing different labels. For example, one may use, alone or in combination, labelling molecules which contain radioactive elements, enzymes and dyes as the labels. Dyes, especially fluorescent dyes, are preferred. Examples of such fluorescent dyes include fluorescein, fluorescein isothiocyanate (FITC), tetramethylrhodamine isothiocyanate (TRITC), phycoerythrin (PE or RD), phycoerythrin-Texas Red conjugates and allophycocyanin.

The application of in situ DNA and RNA hybridization techniques can be used to identify particular cellular characteristics in a similar fashion. In this case, the labelled probes are used to detect the RNA/DNA components associated with a specific disease or condition. G. J. Bauman et al., "Fluorescent In-Situ Hybridization To Detect Cellular RNA By Flow Cytometry And Confocal Microscopy", J. Microscopy 157 (Part 1): 73–81 (January, 1990). "Fluorescent In Situ Hybridization To Interphase Cell Nuclei In Suspension Allows Flow Cytometric Analysis Of Chromosome Content And Microscopic Analysis Of Nuclear Organization", B. Task et al., Human Genetics 78:251–259 (1988). DNA or RNA probes are generally a short oligonucleotide chain complimentary to a chain occurring in the molecule or cell of interest. For example, a DNA probe of sequence GGTATACC would be complimentary to one present in a cell having the sequence CCATATGG.

The control cells expressing a specifically modified antigen can be prepared from leukocyte-rich, anticoagulated blood or from a selected type of cultured cells. In the first instance, a sample of leukocyte-rich, anti-coagulated blood is lysed of red cells (RBCs) and the lysis debris removed by washing. Alternatively, red blood cells may be removed by other suitable means such as the use of an erythrocyte-specific antibody conjugated to an insoluble substrate as described U.S. Pat. No. 4,752,563. If desired, specific types of non-erythrocyte cells can also be removed from the blood sample by the use of additional selective antibodies conjugated to insoluble supports. For example, a monoclonal antibody specific to an antigen present only on granulocytes could be conjugated to an insoluble support and the resulting conjugated antibody used to remove granulocytes from an erythrocyte-free blood sample. Glass, ceramic or polymeric beads, either magnetic or non-magnetic, are among the many types of supports which may be used. Selected cells may also be removed by the use of well known density gradient techniques.

Selected cells can be removed from the original blood sample and these removed cells or the cells remaining in the sample may be activated by means known in the art. For example, some methods of activating cells is discussed in CURRENT PROTOCOLS IN IMMUNOLOGY, J. Coligan, A. Kruisbeek, D. Margulies, E. Shevach and W. Strober, Eds. (Greene Publishing Associated and Wiley-Interscience, New York 1991), Section 3.12 entitled "Proliferative Assays for T Cell Function". After the cells have been activated, they are preserved by the procedures described in U.S. Pat. No. 5,059,518, whose teachings are incorporated herein by reference, or by other suitable preservation techniques known in the art. The principle criterion in the choice of the preservation technique is that the preserved cells, when reconstituted or otherwise readied for actual use in an assay, have retained the antigenicity or other test-relevant characteristics the cells had prior to preservation. The control cells prepared according to this method have present a spectrum of leukocyte cells which exhibit the expression of cellular constituents, including antigenic components, enzyme activity or nucleic acid expression, that is characteristic of and similar to those of leukocyte cells naturally activated in a patient suffering from a disease or disorder. The control cells so prepared are thus suitable for use in clinical and immunological assays which measure leukocyte activation and rely on the characteristics.

Cultured cells from a selected, established cell line can also be used to prepared control cells according to the invention. Cells of the cell line are grown an tissue culture medium using established means, harvested and further processed using chemical or enzymatic procedures to modify the cells' antigenic structure(s). For example, KG1a cells are harvested and treated with iodoactamide to modify the CD34 antigen expression. The modified cells are then added to a leukocyte sample which was produced from leukocyte-rich, anticoagulated blood from which the RBCs and, if desired, other selected cells have been removed by the same techniques as described above. The resulting cell sample may be preserved for use as control cells according to U.S. Pat. No. 5,059,518 or other suitable preservation techniques. The preserved sample containing the modified KG1a cells present a spectrum of leukocyte cells having antigenic modifications similar to those that occur in peripheral blood or bone marrow. When reconstituted or otherwise prepared for use, they are suitable for use as control cells in clinical and immunological assays.

The invention may be carried out in many different forms. That is, many different types of cells from different mammalian species may be prepared for use as control cells. The invention thus has veterinary as well as human applications. The examples given herein are to illustrate the teachings and practice of the invention and are not to be taken as a limitation on the scope of the invention. Therefore, while the examples herein provide for use of human T cells to illustrate the invention, non-T cells or cells from other mammalian species also may be used to prepare control cells useful in the analysis of different diseases in different species.

Figure 11:
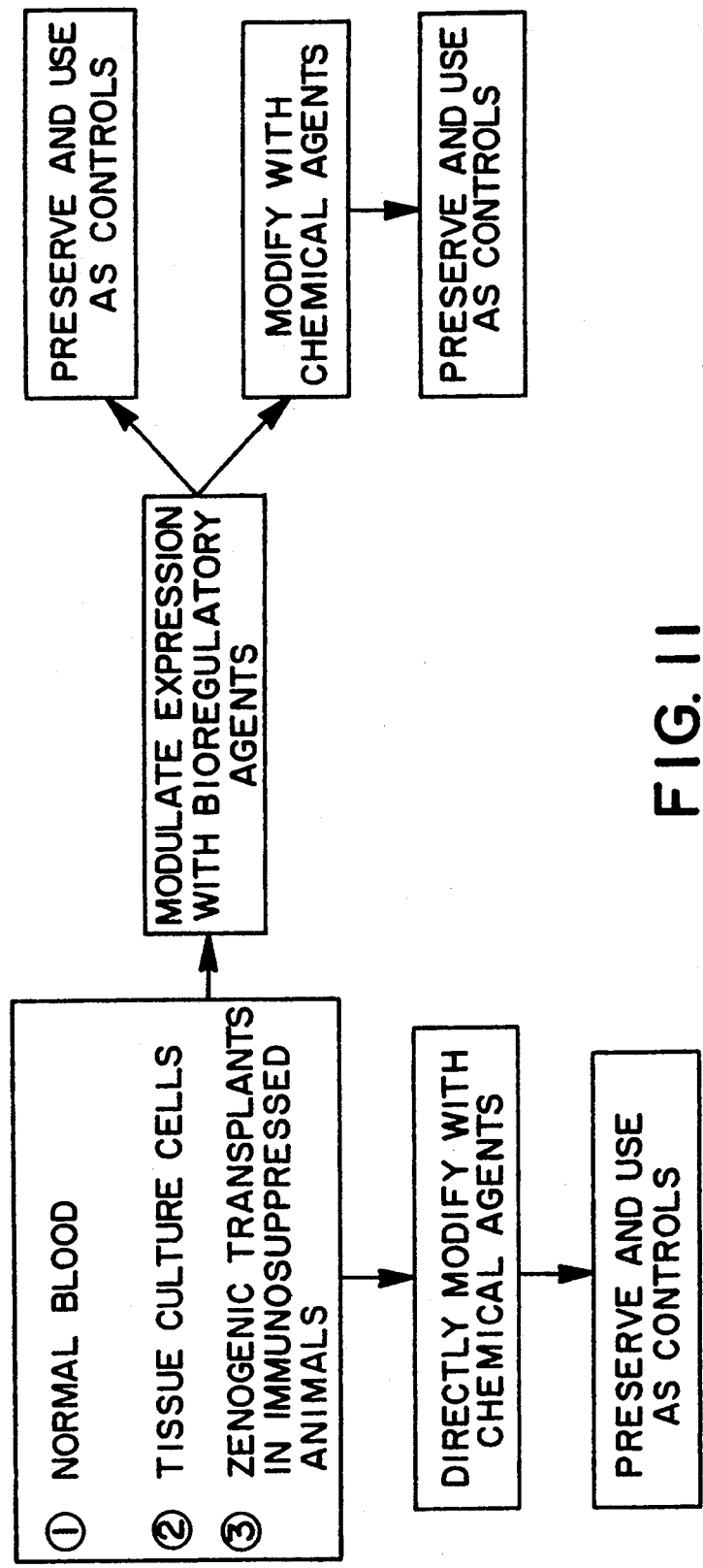
FIG. 11 is a flow chart illustrating the process of modulation or modification of cells for use as abnormal control cells.

FIG. 11 is a flow chart illustrating the various modifications or modulations done to cells prior to their being used as control cells, with or without mixing with other cells, for example, normal cells. Following one path, left-to-right from upper left, normal blood cells, tissue culture cells or zenogenic transplants from immunosuppressed animals are treated with bioregulatory agents. The resulting cells may be either preserved and subsequently used as control cells or they may be further processed using chemical agents before preservation. In the second path, top-to-bottom from upper left, the exemplary cells are only modified before preservation and subsequent use as control cells.

EXAMPLE 1

Control Cells Suitable For Use In An Analysis Of T Cell Activation

T cell activation is an indication of a variety of clinical conditions. The measurement of Type II MHC (DR) antigen is used to determine T cell activation. Preserved, non-infectious control cells containing activated T cells are shown to be useful in an assay measuring T cell activation.

Figure 2:
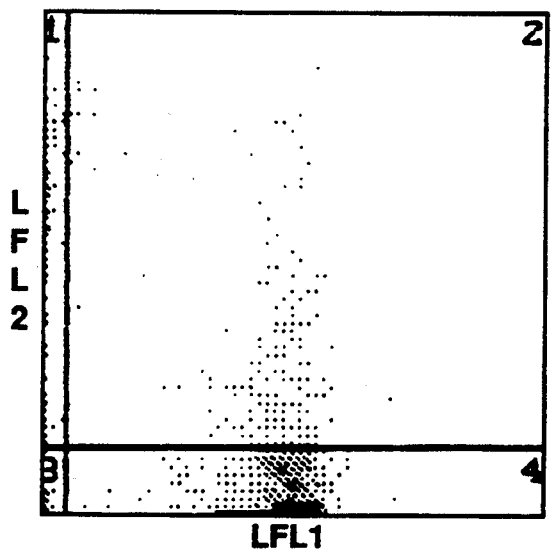
FIG. 2 is a histogram illustrating the distribution of normal peripheral blood lymphocytes cultured for 96 hours without PHA.
Figure 3:
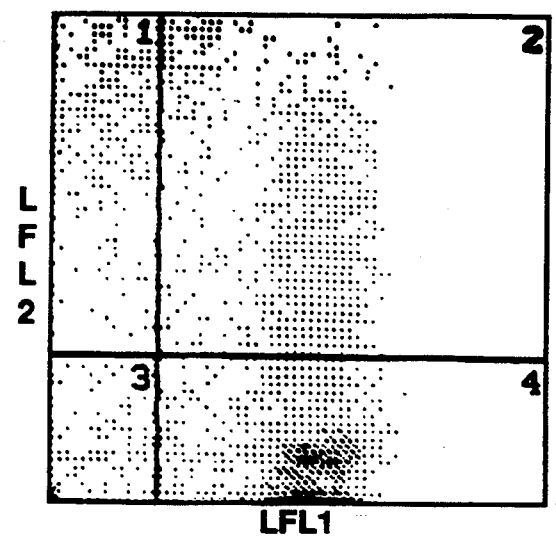
FIG. 3 is a histogram illustrating the distribution of normal peripheral blood lymphocytes activated with $\mu$g/ml PHA for 36 hours, lyophilized and reconstituted before use.

Type II MHC (DR) antigen-modified T cells were prepared from normal, anticoagulated, leukocyte-rich peripheral blood. Several normal, leukocyte-rich blood samples were pooled and the lymphocytes isolated using the density gradient technique in which the blood is diluted with phosphate buffered saline (PBS), layered over Ficoll-Hypaque ® (Pharmacia, Piscataway, N.J.) and centrifuged. Lymphocytes in the interface were removed and washed with in PBS. The washed lymphocytes were then treated with 3 µg/ml phytohemagglutinin (PHA, DIFCO Inc.) and incubated in supplemented RPMI media for about 72–96 hours. At the end of the incubation period, the cells were harvested, washed with PBS or an isotonic 10% trehalose solution, suspended in an isotonic 10% trehalose solution and lyophilized according to U.S. Pat. No. 5,059,518. The preserved control cells, after being reconstituted, were evaluated by comparison with fresh cells. The results are shown in FIGS. 1–3. In these figures, LFL1 represents the fluorescence from an anti-CD3-FITC monoclonal antibody and LFL2 represents the fluorescence from an anti-DR-RD1 monoclonal antibody. Both are obtainable from Coulter Corporation, Hialeah, Fla.

FIG. 1 is a histogram obtained using fresh, that is non-preserved, PHA treated normal peripheral blood lymphocytes. FIG. 2 is a histogram of fresh lymphocytes that were not treated with PHA. FIG. 3 is a histogram of normal peripheral blood lymphocytes treated with PHA (3 µg/ml), lyophilized and reconstituted prior to use as control cells.

FIGS. 1 and 2 demonstrate the increase in the expression of Type II MHC antigen on T cells which have been activated with PHA (FIG. 1, Quad 2) as compared to T cells that have not been activated (FIG. 2, Quad 2). When FIG. 3 is compared with FIGS. 1 and 2, is evident that the control cells, activated and preserved as taught herein show, the same increase in MHC antigen expression (see Quad 2) as seen in FIG. 1, Quad 2.

Figure 9:
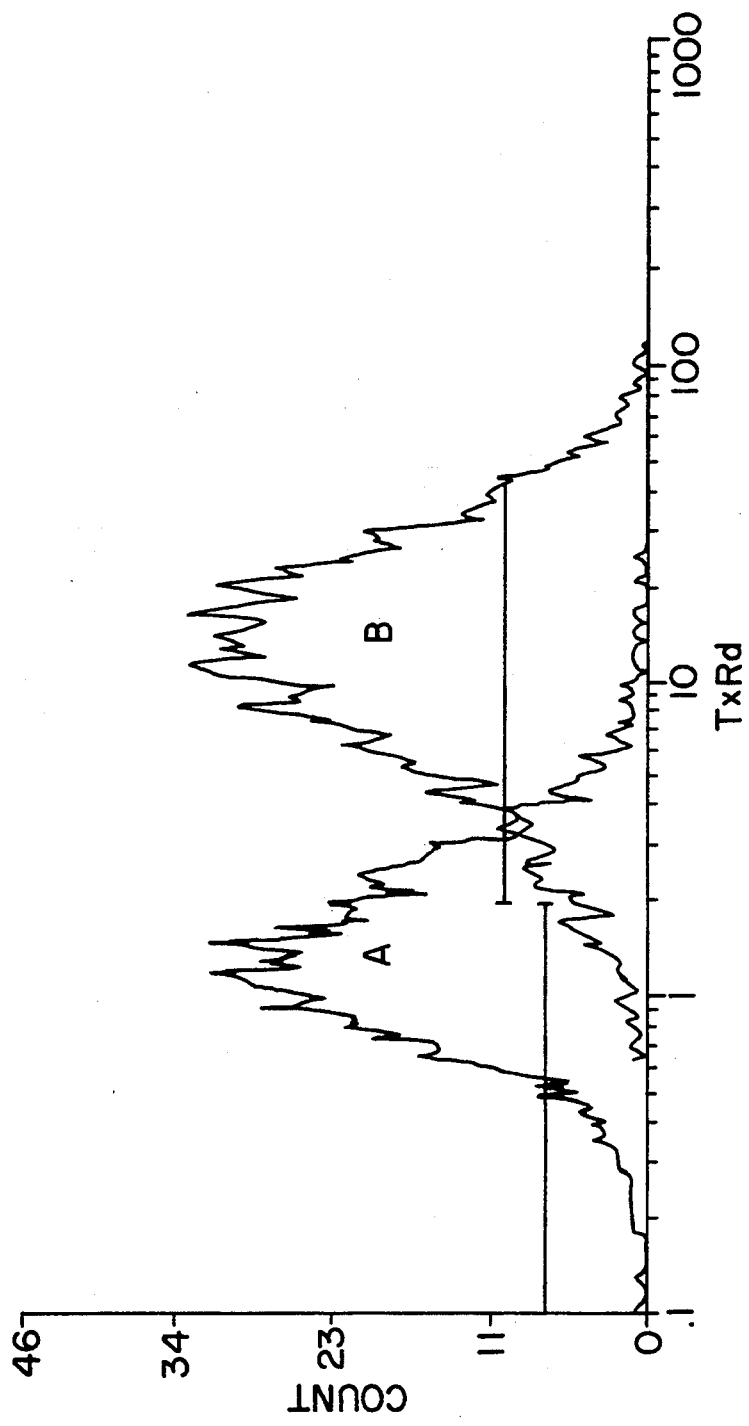
FIG. 9 is an illustration using PHA activated peripheral blood lymphocytes and demonstrating in situ hybridization for the mRNA associated with the cell's production of Interleukin-2.
Figure 10:
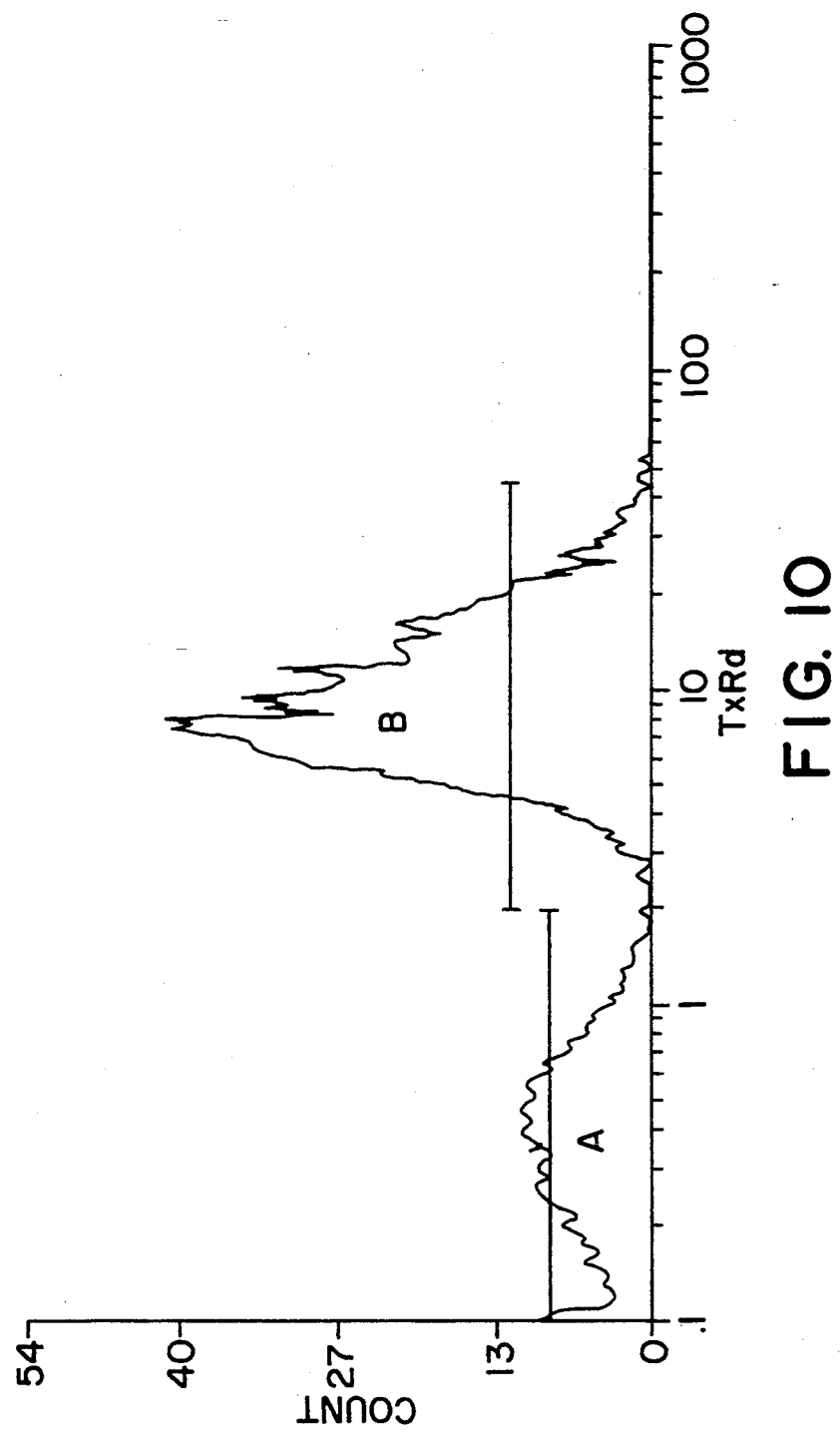
FIG. 10 is an illustration using PHA activated peripheral blood lymphocytes and demonstrating in situ hybridization for the mRNA associated with the cells' production of ICAM-1.

FIGS. 9 and 10 demonstrate the use of labelled oligonucleotide probes to detect changes in cellular mRNA that are associated with cell activation. FIG. 9 is a histogram obtained using fresh (that is, non-preserved) PHA treated normal peripheral blood lymphocytes fixed in 20% acetic-acid, 75% ethanol, 5% water solution for 10 minutes. The fixed cells are then centrifuged at 700 rpm for seven minutes, separated from the supernatant liquid and resuspended in SSC solution (0.15M NaCl, 0.015M sodium citrate, pH 7.0, hereinafter referred to a 1×SCC). A mixture of six biotin labelled anti-sense region specific oligonucleotide probes for human Interleukin-2 mRNA was purchased from British Bio-technology Products Ltd., 4–10 V-Quadrant, Barton Lane, Adington, Oxon OX14 3YS, United Kingdom. Procedures and methods were according to the manufacturer's instruction except that the wash solution used in this procedure comprised 0.4M guanidine thiocyanate, 0.1×SSC solution (the standard 1×solution described above was diluted to one (1) part in 10 ) and 0.1% Triton X-100. Peak A in FIG. 9 is the flow cytometric histogram of normal PBLs. Peak B demonstrates the increase in labelling cells with the Interleukin-2 probes after activation.

FIG. 10 is a flow cytometric histogram obtained in the same manner as the histogram of FIG. 9 except that the region specific oligonucleotide probe cocktail was for human ICAM-1 mRNA. The probes are available from British BioTechnology. Peak A in the histogram shows normal PBLs and Peak B demonstrates the increase in labelling with the ICAM-1 probes after activation.

The following protocol was used for solution hybridization and flow cytometry. These instructions generally follow those supplied by British Bio-technology for the probes described above.

Protocol For Solution Hybridization And Flow Cytometry

A. DEPC-Water Preparation.

Sufficient diethylpyrocarbonate (DEPC) is added to distilled water to give a final concentration of 0.1%. The mixture is shaken well, allowed to stand overnight and autoclaved at sterilizing temperatures and cooled before use. All water used to make the solutions used in this procedure was similarly autoclaved prior to use.

B. Cell Fixation.

1. Dislodge cells and prepare a cell suspension.
2. Wash the suspension with isotonic saline containing 10% trehalose (U.S. Pat. No. 5,059,318, incorporated by reference).
3. Centrifuge at 700 rpm for 7 minutes.
4. Remove supernatant and discard.
5. Suspend the cells in 10 ml of a solution comprising 10% acetic acid, 40% ethanol and 50% water for 10 minutes at room temperature (15°-27° C.). (Note: Other fixing solutions such as the 20% acetic acid, 75% ethanol and 5% water solution described above may also be used.)
6. Centrifuge at 700 rpm for 7 minutes at room temperature.
7. Re-suspend cells in 1 ml of 2×SCC buffer (twice concentration of 1×SCC).

C. Hybridization.
1. Use 0.1 ml of cell suspension, containing $1$–$50 \times 10^6$ cells, for each hybridization.
2. Spin cells to form a pellet and remove supernatant liquid.
3. Re-suspend cells in 50 μL of hybridization cocktail that has been denatured by heating for 5 minutes at 95° C. The hybridization cocktail comprises:
   50% Formamide
   600 mM NaCl
   Sheared Salmon Sperm DNA (prepared by adding 100 mg of salmon sperm DNA to 10 ml of sterile distilled water and letting the sperm DNA dissolve overnight at 4° C. Shearing is done by sonication).
   1×PE solution (prepared by dilution of a 10×PE solution that is prepared by dissolving the following at 65° C.).

| (a) Tris-HCL, pH 7.5 | 0.5 M |
| (b) Sodium pyrophosphate | 1% w/v |
| (c) Polyvinylpyrolidone (MW 40K) | 2% w/v |
| (d) Ficoll (MW 400K) | 2% w/v |
| (e) EDTA (disodium) | 50 mM |

4. Hold the suspension of 3 for 2 hours at 42° C.
5. Place the suspension in a 50 ml conical table and add 25 ml of a solution containing 0.4M guanidine thiocyonate, 1×SSC and 0.1% Triton X-100.
6. Centrifuge for 10 minutes at 2500 rpm.
7. Remove the supernatant liquid and add 25 ml of a solution comprising 0.1×SSC and 0.1% Triton X-100 to resuspend the cells.
8. Centrifuge for 10 minutes at 2500 rpm and remove the supernatant liquid, incubate with 1:1,000 Avidin-FITC (Veclor, USA) for 15 minutes at 22° C. Add 1 ml Isoton III (Coulter, Miami, Fla.), centrifuge for 10 minutes at 2500 rpm and remove the supernatant liquid.
9. Resuspend the cells in 0.3 ml of Isoton III or equivalent for use in the flow cytometer.

EXAMPLE 2

Control Cells Suitable For Use In An Analysis of CD34 Positive Cells

The CD34 positive cells of normal, non-diseased donors are associated with levels of hematopoietic progenitor cells and are related to the functioning of bone marrow cells. However, the low frequency (number or count) of these cells in a normal blood sample makes their detection and enumeration difficult. Some diseases manifest themselves early-on by a change in the level of CD34 positive cells. Consequently, it is desirous to have a available control cells which aid in the confirming the detection of CD34 positive cells and in their enumeration.

CD34 positive cells were obtained from the ATCC in the form of a sample of Deposit No. CCL246 1, the KG1 a cell line. The KG1a cells of the sample were cultured, harvested and placed in a chemical modifying medium (CMM) comprising of an isotonic solution containing iodoacetamide (10 mg per 50 ml), levanisole (200 ml per liter), phenylmethylsulfonyl fluoride (1 μg/ml) and 0.1% sodium azide. The cells were then incubated for a time in the range of about 1–5 hours, and preferably about 1–3 hours. The degree of chemical modification to the KG1a cell line is directly proportional to length of the incubation period.. After incubation, the cells were washed once with isotonic 10% trehalose solution and placed in 0.5% paraformaldehyde solution for about 12 hours. The chemically modified KG1a cells were isolated from the paraformaldehyde solution by centrifuging and were suspended in isotonic 10% trehalose solution for use in the next step.

In the next step, non-infectious leukocytes were prepared by first pooling a plurality of normal, anticoagulated leukocyte-rich blood packs and lysing the red blood cells. After lysis, the leukocyte cells were washed a plurality of times with Hepes buffered saline (HBS). The leukocyte cells were then separated from the final wash and placed in a vessel with isotonic 10% trehalose solution. The chemically modified KG1a cells were then added to noninfectious normal leukocytes and resulting mixture lyophilized to produce preserved control cells suitable for use in a CD34 assay. Before use in such an assay the control cells were reconstituted in distilled water. The control cells were evaluated flow cytometrically using fluorescently labelled monoclonal antibodies. FIGS. 4–8 represent a comparison of analytical results obtainable using control cells prepared and preserved according to the invention and fresh CD34 positive cells obtained from a patient.

Figure 4:
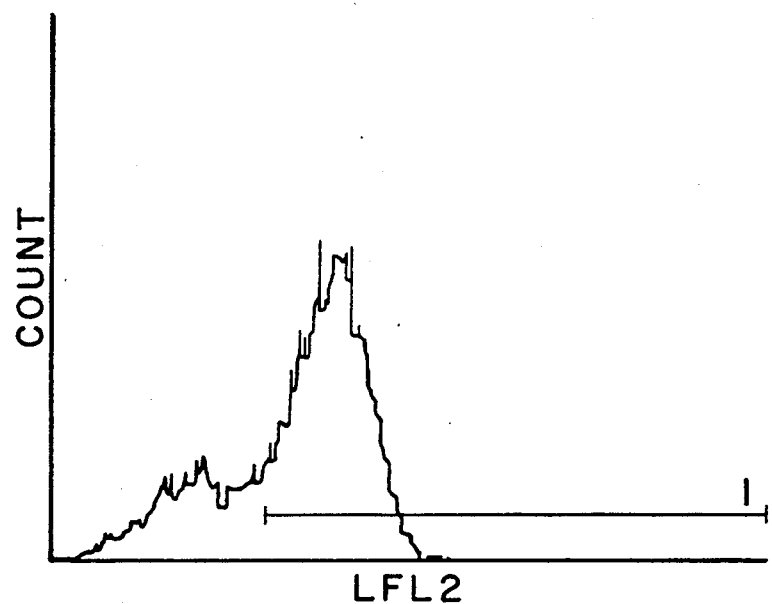
FIG. 4 illustrates the distribution and count of CD34 positive leukocytes in the peripheral blood of a patient with acute myelogenous leukemia (AML).

FIG. 4 depicts the CD34 positive leukocytes in the peripheral blood of a patient suffering from AML. LFL2 represents the fluorescence from cells conjugated to an anti-CD34-PE monoclonal antibody (Becton-Dickinson Immunology Systems, San Jose, Calif.). CD34 positive cells above the background level are indicated by histogram gate No. 1.

Figure 5:
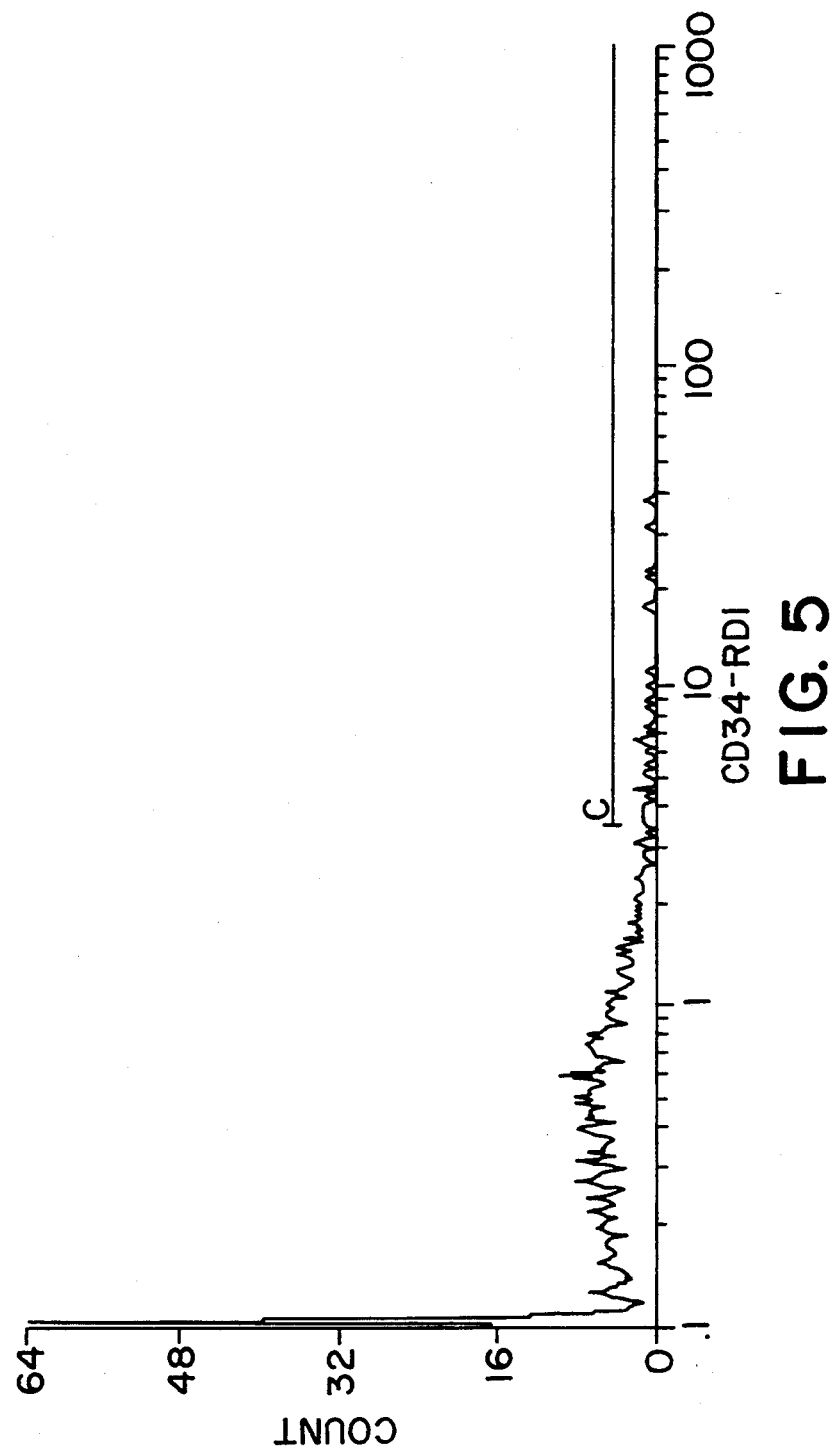
FIG. 5 illustrates the distribution and count of CD34 positive bone marrow cells in a normal bone marrow sample.

FIG. 5 depicts the CD34 positive cells in a normal bone marrow sample. The x-axis of the histogram represents the fluorescence from cells conjugated to an anti-CD34-RD1 monoclonal antibody (Coulter Corporation). Based on isotype control, histogram gate "C" indicates the positive cells above background level.

Figure 6:
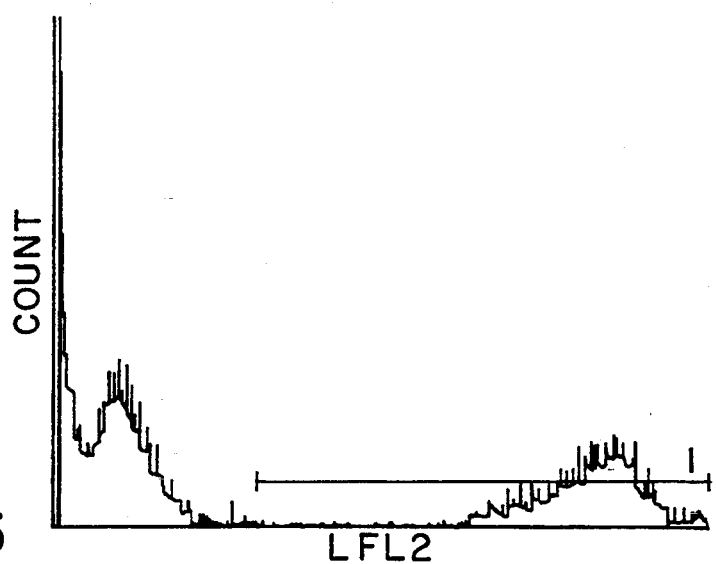
FIG. 6 illustrates the distribution and count of lyophilized CD34 positive KG1a tissue culture cells mixed with normal peripheral blood lymphocytes.

FIG. 6 depicts reconstituted lyophilized control cells consisting of CD34 positive KG1a tissue culture cells that have been mixed with normal peripheral blood lymphocytes prior to lyophilization. LFL2 represents the fluorescence from cells conjugated with an anti-CD34-PE monoclonal antibody (Becton-Dickinson). CD34 positive cells above the background level are indicated by histogram gate number 1. The level of fluorescence indicated by "mean" represents the degree of expression of the anti-CD34 monoclonal antibody binding capacity.

Figure 7:
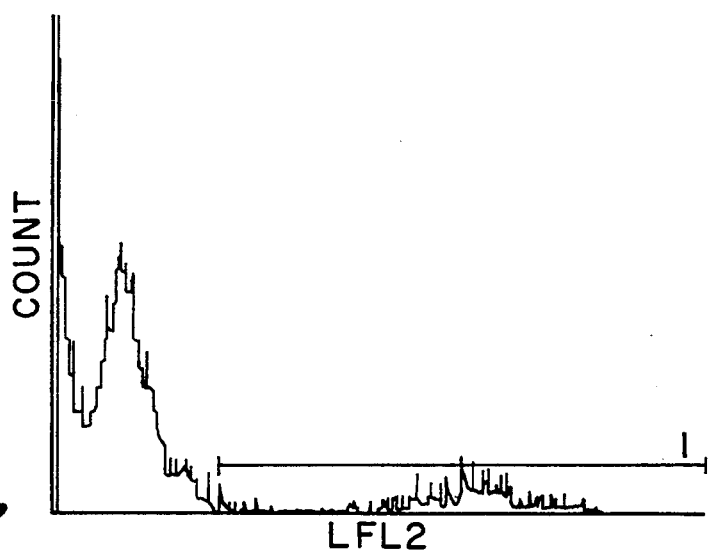
FIG. 7 illustrates the distribution and count of reconstituted, lyophilized, chemically modified CD34 positive KG1a tissue culture cells mixed with normal peripheral blood lymphocytes.

FIG. 7 depicts reconstituted lyophilized control cells consisting of chemically modified CD34 positive KG1a tissue culture cells that were mixed with normal peripheral blood lymphocytes before lyophilization. LFL2 represents the fluorescence of those cells conjugated to an anti-CD34-PE monoclonal antibody (Becton-Dickinson). CD34 positive cells above the background level are indicated by histogram gate number 1. The level of fluorescence indicated by the "mean" channel (155) presents the reduced degree of expression of the anti-CD34 monoclonal antibody binding capacity that occurs after chemical modification.

Figure 8:
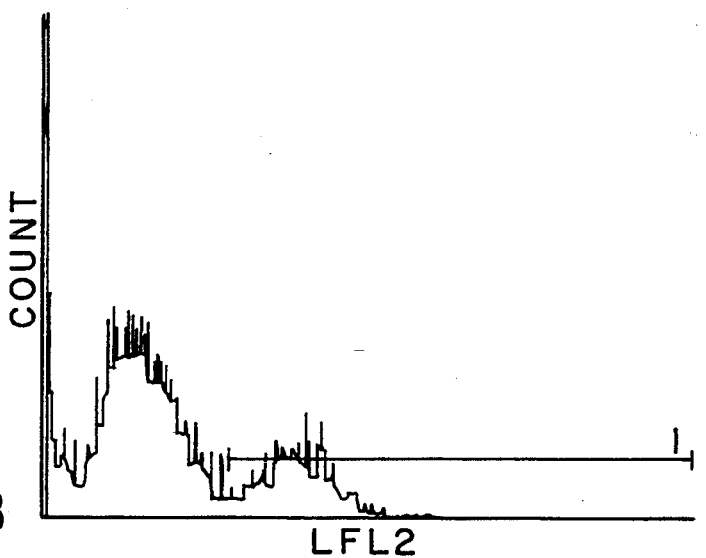
FIG. 8 is a second illustration of the distribution and count of reconstituted chemically modified CD34 positive KG1a tissue cells mixed with normal peripheral blood lymphocytes.

FIG. 8 depicts reconstituted lyophilized control cells consisting of chemically modified CD34 positive KG1a tissue culture cells mixed with normal peripheral blood lymphocytes prior to lyophilization. LFL2 represents the fluorescence of those cells that are conjugated to an anti-CD34-PE monoclonal antibody (Becton-Dickinson). CD34 positive cells above the background level are indicated by histogram gate 1. The level of fluorescence indicated by the "mean" channel represents a further reduction of the degree of expression of anti-CD34 monoclonal antibody binding after increased chemical modification by extending the incubation period over that for the sample of FIG. 7.

FIGS. 6–8 compare normal lymphocytes which have been augmented with non-modified CD34 positive KG1a cells (FIG. 6) with normal lymphocytes that have been augmented with KG1a cells that have chemically modified to express different degrees of CD34 antigen expression. The results in FIG. 6 represent the baseline. That is, if the percentage of KG1a cells is constant in the samples represented by FIGS. 6–8, the number of cells expressing the CD34 antigen will be greatest in FIG. 6. Chemical modification of the KG1a cells destroys the expression of the CD34 antigen as indicated by a reduction in mean Tables 6–8. FIGS. 7–8 represent samples with the reduced expression.

The results shown herein by FIGS. 1–8 indicate that the method of the invention can be used to prepare lyophilized, non-infectious control cells which contain differing levels of CD34 expression and that these control cells, when reconstituted, can be used in clinical and immunological assays.

The following data tables correspond to the indicated figures.

TABLE 1

FIG. 1.

|   |   | MIN | MAX | COUNT | PER-CENT | MEAN | SD | % HPCV |
|---|---|-----|-----|-------|----------|------|-----|--------|
| 1 | X | 0   | 10  | 260   | 5.2      | 4.3  | 3.5 |        |
|   | Y | 7   | 63  |       |          | 36.6 | 16.8| 1.54   |
| 2 | X | 11  | 63  | 2943  | 58.9     | 29.3 | 5.9 | 13.9   |
|   | Y | 7   | 63  |       |          | 25.6 | 12.5| 37.2   |
| 3 | X | 0   | 10  | 177   | 3.5      | 2.3  | 3.5 |        |
|   | Y | 0   | 6   |       |          | 1.0  | 1.8 |        |
| 4 | X | 11  | 63  | 1619  | 32.4     | 29.5 | 5.6 | 10.9   |
|   | Y | 0   | 6   |       |          | 1.1  | 1.9 |        |

TABLE 2

FIG. 2.

|   |   | MIN | MAX | COUNT | PER-CENT | MEAN | SD | % HPCV |
|---|---|-----|-----|-------|----------|------|-----|--------|
| 1 | X | 0   | 2   | 188   | 3.8      | 0.1  | 0.4 |        |
|   | Y | 9   | 63  |       |          | 36.6 | 11.1| 5.75   |
| 2 | X | 3   | 63  | 200   | 4.0      | 28.1 | 6.7 | 7.41   |
|   | Y | 9   | 63  |       |          | 20.1 | 12.2| 14.7   |
| 3 | X | 0   | 2   | 365   | 7.3      | 0.0  | 0.2 |        |

TABLE 2-continued

FIG. 2.

|   |   | MIN | MAX | COUNT | PER-CENT | MEAN | SD | % HPCV |
|---|---|-----|-----|-------|----------|------|-----|--------|
|   | Y | 0   | 8   |       |          | 1.1  | 2.0 |        |
| 4 | X | 3   | 63  | 4246  | 84.9     | 29.5 | 3.4 | 8.14   |
|   | Y | 0   | 8   |       |          | 1.0  | 2.0 |        |

TABLE 3

FIG. 3

|   |   | MIN | MAX | COUNT | PER-CENT | MEAN | SD | % HPCV |
|---|---|-----|-----|-------|----------|------|-----|--------|
| 1 | X | 0   | 13  | 432   | 8.6      | 5.7  | 4.7 |        |
|   | Y | 19  | 63  |       |          | 50.1 | 10.3|        |
| 2 | X | 14  | 63  | 1255  | 25.1     | 31.1 | 6.6 | 10.1   |
|   | Y | 19  | 63  |       |          | 36.4 | 12.2| 32.5   |
| 3 | X | 0   | 13  | 260   | 5.2      | 5.1  | 4.8 |        |
|   | Y | 0   | 18  |       |          | 3.7  | 4.9 |        |
| 4 | X | 14  | 63  | 3052  | 61.1     | 32.2 | 5.3 | 12.3   |
|   | Y | 0   | 18  |       |          | 4.0  | 4.7 |        |

TABLE 4

FIG. 4

|   | MIN | MAX | COUNT | PER-CENT | MEAN | SD | % HPCV |
|---|-----|-----|-------|----------|------|-----|--------|
| 1 | 7.960 | 1023. | 6991 | 69.9 | 14.95 | 1.47 | 12.6 |

TABLE 6

FIG. 6

|   | MIN | MAX | COUNT | PER-CENT | MEAN | SD | % HPCV |
|---|-----|-----|-------|----------|------|-----|--------|
| 1 | 78  | 255 | 1176  | 33.6     | 206.8| 25.0| 4.22   |

TABLE 7

FIG. 7

|   | MIN | MAX | COUNT | PER-CENT | MEAN | SD | % HPCV |
|---|-----|-----|-------|----------|------|-----|--------|
| 1 | 65  | 255 | 574   | 16.4     | 155.2| 34.0| 0.85   |

TABLE 8

FIG. 8

|   | MIN | MAX | COUNT | PER-CENT | MEAN | SD | % HPCV |
|---|-----|-----|-------|----------|------|-----|--------|
| 1 | 72  | 255 | 820   | 23.4     | 99.4 | 14.8| 1.40   |

We claim:

1. Control cells composition for use in clinical and immunological assays, utilizing flow cytometry comprising a preserved mixture of (a) normal mammalian leukocyte cells and (b) selected normal mammalian leukocyte cells which have been artificially enzymatically or chemically activated or modified to express antigenic characteristics expressed on the same leukocyte cells in a person having a disease or disorder which results in the expression of said characteristics on said selected leukocyte cells; said mixture is preserved by lyophilization with an isotonic trehalose solution.

2. The control cell composition of claim 1 wherein the ac-tivated or modified leukocyte cells of part (b) consist of a subset of the normal leukocyte cells of part (a) which have been activated or modified.

3. The control cell composition according to claim 1 wherein said activated or modified cells are T and B cells.

4. The control cell composition according to claim 1 wherein said activated or modified cells are T cells.

5. The control cell composition according to claim 1 wherein said cells are suitable for replacing fresh abnormal mammalian cells as standards in cell flow cytometric analysis.

6. Control cell composition for clinical and immunological flow cytometry assays comprising a mixture preserved with isotonic trehalose of the following which are suitable for use in flow cytometry assays:
(a) normal mammalian leukocyte cells; and
(b) normal mammalian cells which have been artificially inhibited during an incubation period, of modified, or activated, so as to possess antigenic characteristics expressed on the same type of cells in a person having a disease of disorder which results in the expression of said characteristics on said cells.

7. The control cell composition of claim 6 wherein the cells of part (b) are T cells, B cells and tissue cells.

8. A process for preparing a mixture of preserved mammalian control cells useful in flow cytometry analysis in which a selected population of leukocyte cells in a normal leukocyte cell population have been artificially activated or modified to express antigenic characteristics which are expressed on the same leukocyte cells in a person having a disease or disorder, said process comprising:
(a) incubating a sample of normal leukocyte cells in a medium with an enzyme or chemical reagent in order to selectively activate or modify the antigenic characteristics of a selected population of leukocyte cells such that said selected population of cells has characteristics which are representative of the same cells taken from a patient suffering from a disease or disorder;
(b) separating the leukocyte cells, which now include the activated or modified selected population of leukocyte cells, from the medium and washing the separated cells; and
(c) preserving the washed cells by lyophilization with an isotonic trehalose solution so that when they are reconstituted, the cells can be used an control cells in immunological assays including flow cytometry assays.

9. A process for preparing a mixture of preserved mammalian control cells useful in flow cytometry analysis in which a selected population of leukocyte cells in a normal leukocyte cell population have been artificially activated or modified to express antigenic characteristics which are expressed on the same leukocyte cells in a person having a disease of disorder, comprising:
(a)(i) separating the total leukocyte population in order to obtain a selected population of leukocyte cells and the remaining leukocyte cells;
(ii) separately retaining both the selected population of leukocyte cells and the remaining cells;
(iii) artificially activating or modifying the selected population of leukocyte cells with an enzyme or chemical reagent in a medium;
(b)(1) separating the activated or modified population of leukocyte cells from the medium and washing the same; and
(ii) mixing the washed, activated or modified population of leukocyte cells with the remaining leukocyte cells; or alternatively, mixing the washed, activated or modified leukocyte cells with the remaining leukocyte cells and other non-activated or unmodified leukocyte cells, in an amount representative of a stage of the disease; and
(c) preserving the washed cells by lyophilization with an isotonic trehalose solution so that when they are reconstituted, the cells can be used as control cells in immunological assays including flow cytometry assays.

* * * * *